United States Patent
Brächer et al.

(10) Patent No.: US 11,834,399 B2
(45) Date of Patent: Dec. 5, 2023

(54) OPTIMIZED THERMAL SEPARATION BY PRIOR GAS EXCHANGE

(71) Applicant: Evonik Operations GmbH, Essen (DE)

(72) Inventors: Alexander Brächer, Haltern am See (DE); Ana Markovic, Haltern am See (DE); Anna Chiara Sale, Recklinghausen (DE); Dirk Fridag, Haltern am See (DE); Johannes Knossalla, Gahlen (DE); Peter Kucmierczyk, Herne (DE); Robert Franke, Marl (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/165,245

(22) Filed: Feb. 6, 2023

(65) Prior Publication Data
US 2023/0250040 A1    Aug. 10, 2023

(30) Foreign Application Priority Data
Feb. 8, 2022 (EP) .................................... 22155546

(51) Int. Cl.
| | | |
|---|---|---|
| *C07C 45/50* | (2006.01) | |
| *B01J 31/18* | (2006.01) | |
| *C07C 45/77* | (2006.01) | |
| *C07C 45/78* | (2006.01) | |

(52) U.S. Cl.
CPC ............ *C07C 45/77* (2013.01); *B01J 31/1845* (2013.01); *C07C 45/786* (2013.01)

(58) Field of Classification Search
CPC ........ C07C 45/50; C07C 45/786; B01D 71/52
See application file for complete search history.

(56) References Cited

U.S. PATENT DOCUMENTS

| | | | | |
|---|---|---|---|---|
| 8,226,829 | B2 * | 7/2012 | Wiese | B01D 61/027 568/426 |
| 8,969,628 | B2 * | 3/2015 | Priske | B01J 31/4046 568/426 |
| 10,501,392 | B2 * | 12/2019 | Fridag | C07C 29/175 |
| 10,633,302 | B2 * | 4/2020 | Nadolny | B01J 37/0201 |
| 10,647,650 | B2 * | 5/2020 | Hecht | B01J 23/464 |
| 10,654,784 | B2 * | 5/2020 | Haßelberg | C07C 45/50 |
| 10,850,261 | B2 * | 12/2020 | Nadolny | B01J 23/02 |
| 10,882,027 | B2 * | 1/2021 | Nadolny | B01J 35/1019 |
| 11,008,275 | B2 * | 5/2021 | Kucmierczyk | C07C 67/02 |
| 11,396,488 | B2 * | 7/2022 | Brächer | C07C 45/505 |

FOREIGN PATENT DOCUMENTS

| | | |
|---|---|---|
| EP | 3945085 | 2/2022 |
| FR | 1008045 | 5/1952 |
| GB | 702242 | 1/1954 |
| WO | 2007/133379 | 11/2007 |

OTHER PUBLICATIONS

European Search Report dated Jun. 9, 2023, in European Patent Application No. 23152830.8, 7 pages.

* cited by examiner

*Primary Examiner* — Sikarl A Witherspoon
(74) *Attorney, Agent, or Firm* — Grüneberg and Myers PLLC

(57) ABSTRACT

A process can be used for preparing aldehydes from C2 to C20 olefins with a subsequent thermal separation for removal of the aldehyde formed. The process involves a membrane separation, which is preceded by performance of a gas exchange by which the proportion of the partial pressure represented by carbon monoxide or hydrogen is increased in order to reduce catalyst losses.

20 Claims, No Drawings

OPTIMIZED THERMAL SEPARATION BY PRIOR GAS EXCHANGE

CROSS-REFERENCE TO RELATED APPLICATIONS

This application claims priority to European Application No. 22155546.9, filed on Feb. 8, 2022, the content of which is hereby incorporated by reference in its entirety.

BACKGROUND OF THE INVENTION

Field of the Invention

The present invention provides a process for preparing aldehydes from C2 to C20 olefins with a subsequent thermal separation for removal of the aldehyde formed, wherein the membrane separation is preceded by performance of a gas exchange by which the proportion of the partial pressure represented by carbon monoxide or hydrogen is increased in order to reduce catalyst losses.

Description of Related Art

Hydroformylation processes for preparing aldehydes have long been known to those skilled in the art. In these processes, olefins are converted into the corresponding aldehydes by reaction with syngas, a mixture of carbon monoxide (CO) and hydrogen ($H_2$), in the presence of a catalyst system. Hydroformylation is a process employed in industry in plants capable of producing hundreds of kilotonnes (kt) of aldehyde per year. Catalyst systems typically used here are homogeneously dissolved catalyst systems and comprise transition metal complexes of mostly cobalt or rhodium as metal and phosphorus ligands.

The ability to economically operate such hydroformylation processes on a scale of hundreds of kt depends on various factors. One important factor is the metal in the homogeneously dissolved catalyst system, since rhodium and cobalt and compounds thereof employed as catalyst precursor are relatively costly raw materials. A core objective in the operation of industrial hydroformylation processes is accordingly the minimization of catalyst losses during operation.

Catalyst losses can occur in thermal separation processes. Thermal separation in the context of the present invention means a separation process in which separation is effected on the basis of the boiling point. Thermal separation processes may especially be used for separation of the products formed from the reaction solution. The catalyst losses that occur in the process may be caused, for example, by adhesion of clusters in parts of the plant or by the precipitation of insoluble transition metal compounds in the plant.

SUMMARY OF THE INVENTION

The problem addressed by the present invention was therefore that of providing a process for preparing aldehydes, in which the catalyst losses in the thermal removal are reduced compared to known processes.

It has been found that, surprisingly, this problem is solved by conducting a gas exchange after the actual reaction, but before the thermal separation. In this process, the syngas, that is to say a mixture comprising mainly carbon monoxide and hydrogen, is at least partially replaced by carbon monoxide or hydrogen, as a result of which the proportion of the partial pressure represented by carbon monoxide or hydrogen is increased. By comparison with the reaction, the product-containing reaction output is thus contacted with a gas of different composition or with a different gas mixture, which results in a reduction in catalyst loss in the subsequent thermal separation.

The problem is accordingly solved in accordance with the invention by a process for preparing aldehydes, wherein the process comprises at least the following steps:
a) hydroformylation by reaction of C2 to C20 olefins with synthesis gas in the presence of a homogeneously dissolved catalyst system comprising at least one metal from the group consisting of Co and Rh, and a phosphorus ligand, wherein the hydroformylation is conducted in at least one reaction zone and at a pressure of 15 to 350 bar absolute, which affords a liquid reaction output containing at least the aldehydes formed and unconverted olefins, and in which the partial pressure of CO or $H_2$ accounts for at most 70% of the total gas pressure, i.e. the sum total of the pressures of all the gaseous substances present;
b) performing a gas exchange with the liquid reaction output, which affords a liquid reaction output in which the partial pressure of CO or $H_2$ accounts for more than 90% of the total gas pressure, preferably more than 95% of the total gas pressure, more preferably more than 98% of the total gas pressure;
c) single-stage or multistage expansion of the liquid reaction output obtained from step b) to a pressure of less than 1 bar absolute;
d) feeding the liquid reaction output expanded in step c) to a thermal separation in order to separate the reaction output into a low-boiling and a high-boiling fraction, with the low-boiling fraction containing at least a portion of the aldehydes.

The invention also includes the following embodiments:
1. Process for preparing aldehydes, wherein the process comprises at least the following steps:
   a) hydroformylation by reaction of C2 to C20 olefins with synthesis gas in the presence of a homogeneously dissolved catalyst system comprising at least one metal from the group consisting of Co and Rh, and a phosphorus ligand, wherein the hydroformylation is conducted in at least one reaction zone and at a pressure of 15 to 350 bar absolute, which affords a liquid reaction output containing at least the aldehydes formed and unconverted olefins, and in which the partial pressure of CO or $H_2$ accounts for at most 70% of the total gas pressure, i.e. the sum total of the pressures of all the gaseous substances present;
   b) performing a gas exchange with the liquid reaction output, which affords a liquid reaction output in which the partial pressure of CO or $H_2$ accounts for more than 90% of the total gas pressure, preferably more than 95% of the total gas pressure, more preferably more than 98% of the total gas pressure;
   c) single-stage or multistage expansion of the liquid reaction output obtained from step b) to a pressure of less than 1 bar absolute;
   d) feeding the liquid reaction output expanded in step c) to a thermal separation in order to separate the reaction output into a low-boiling and a high-boiling fraction, with the low-boiling fraction containing at least a portion of the aldehydes.
2. Process according to embodiment 1, wherein the hydroformylation in step a) is conducted at a pressure of 10 to 350 bar absolute.

3. Process according to embodiment 1 or 2, wherein the homogeneously dissolved catalyst system used in step a) comprises at least Rh and a phosphorus ligand.
4. Process according to any of the preceding embodiments, wherein the gas exchange in step c) is effected by expanding the liquid reaction output and subsequently injecting CO or $H_2$ until the desired partial pressure of CO or $H_2$ is attained.
5. Process according to embodiment 4, wherein the expansion of the liquid reaction output and the subsequent injection of CO or $H_2$ are effected in repeated succession.
6. Process according to any of the preceding embodiments, wherein the hydroformylation is conducted at a temperature of 80° C. to 250° C.
7. Process according to any of the preceding embodiments, wherein the total gas pressure after the gas exchange is 1 to 70 bar absolute, preferably 2 to 30 bar absolute, preferably 4 to 20 bar absolute.
8. Process according to any of the preceding embodiments, wherein the thermal separation is conducted at a temperature of 20° C. to 200° C., preferably between 50° C. and 160° C.
9. Process according to any of the preceding embodiments, wherein the thermal separation comprises at least one thermal separation process selected from the group consisting of thin-film evaporation, distillation, flash evaporation, falling-film evaporation and short-path evaporation.
10. Process according to any of the preceding embodiments, wherein the process is conducted continuously.
11. Process according to any of the preceding embodiments, wherein the reaction zone comprises at least one reactor.
12. Process according to any of the preceding embodiments, wherein the thermal separation is preceded or followed by performance of at least one membrane separation.
13. Process according to embodiment 12, wherein the thermal separation is followed by injection of CO or $H_2$ onto the liquid reaction output depleted of the aldehydes formed until the partial pressure of CO or $H_2$ accounts for more than 90% of the total gas pressure, preferably more than 95% of the total gas pressure, more preferably more than 98% of the total gas pressure.
14. Process according to embodiment 12 or 13, wherein a membrane material used in the membrane separation is selected from the group consisting of poly(dimethylsiloxane)s, polyimides, partially fluorinated polymers, completely fluorinated polymers, perfluorinated polymers, amorphous fluoropolymers (e.g. Cytop), amorphous or partially crystalline perfluoroalkoxy polymers (e.g. Hyflon), block copolymers of the abovementioned materials, polymers having intrinsic microporosity (PIM), poly(aryletherketone)s, in particular poly(etheretherketone)s and poly(etherketoneketone)s, polybenzimidazoles and polyethers.
15. Process according to embodiment 14, wherein a membrane material is used that is intrinsically stable in the reaction output/in the mixture present after the thermal separation, i.e. does not require any additional crosslinking of the polymer chains.

DETAILED DESCRIPTION OF THE INVENTION

The pressure values stated in this application are all reported in "bar absolute". By definition, bar absolute is a figure for absolute pressure, i.e. pressure with respect to zero pressure in an empty space (vacuum).

Step a) of the process of the invention is the hydroformylation of C2-C20 olefins, preferably C2 to C17 olefins, more preferably C3 to C14 olefins and most preferably C6 to C14 olefins. In principle, the pure olefins may be used in the process. Preference is however given to using hydrocarbon streams comprising the appropriate olefins. The olefin content of the hydrocarbon streams should naturally be sufficiently high for it to be possible to operate a hydroformylation economically. The olefin-containing feedstock mixtures preferably contain practically no further unsaturated compounds or polyunsaturated compounds such as dienes or acetylene derivatives.

The hydrocarbon streams that can be used in the process of the invention may comprise olefins having terminal and/or internal carbon-carbon double bonds. The hydrocarbon streams mentioned may also comprise olefins having the same number or different numbers of carbon atoms. Suitable olefins are in particular ethene, propene, 1- or 2-butene or mixtures thereof, isobutene, 1- or 2-pentene or mixtures thereof, isopentene, 1-, 2- or 3-hexene, 1-heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctene, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond and mixtures of linear hexadecenes.

Propylene is produced industrially by the cracking of naphtha and is a basic chemical that is readily available. C5 olefins, i.e. pentenes, are present in light petroleum fractions from refineries or crackers. Technical mixtures comprising linear C4 olefins, n-butene and isobutene are light petroleum fractions from refineries, C4 fractions from FC crackers or steam crackers, mixtures from Fischer-Tropsch syntheses, mixtures from the dehydrogenation of butanes, and mixtures resulting from metathesis or other industrial processes. For example, mixtures of linear butenes suitable for the process of the invention are obtainable from the C4 fraction of a steam cracker.

The higher olefins can in particular be obtained by oligomerization reactions, for example dimerization, trimerization or tetramerization. Suitable hydrocarbon streams are in addition the mixture of isomeric hexenes (dipropene) resulting from the dimerization of propene, the mixture of isomeric octenes (dibutene) resulting from the dimerization of butenes, the mixture of isomeric nonenes (tripropene) resulting from the trimerization of propene, the mixture of isomeric dodecenes (tetrapropene or tributene) resulting from the tetramerization of propene or the trimerization of butenes, the isomeric hexadecenes (tetrabutene) resulting from the tetramerization of butenes and also the olefin mixtures produced by the co-oligomerization of olefins having a varying number of carbon atoms (preferably 2 to 4 carbon atoms), optionally after distillative separation into fractions having the same or different numbers of carbon atoms. Olefins or olefin mixtures produced by Fischer-Tropsch synthesis may also be used. It is additionally possible to use olefins produced by olefin metathesis or by other industrial processes.

The olefins used in the process are hydroformylated with syngas in the presence of a homogeneously dissolved catalyst system. The molar ratio between syngas and the feedstock mixture should be between 6:1 and 1:1, preferably between 3:1 and 1:1, more preferably between 2:1 and 1:1. The hydroformylation may optionally be carried out in the presence of a solvent known to those skilled in the art, but it is preferable to use no solvent.

The homogeneous catalyst system used in the process of the invention comprises or consists of Co or Rh, preferably Rh, and preferably a phosphorus ligand. In a particularly preferred embodiment, the catalyst system of the invention comprises or consists of Rh and a phosphorus ligand. Suitable ligands for the catalyst systems of the invention are known to those skilled in the art (see e.g. the textbooks "Rhodium Catalyzed Hydroformylation" (from 2002) by P.W.N.M. van Leeuwen or "Hydroformylation—Fundamentals, Processes and Applications in Organic Synthesis" (from 2016) by A. Borner and R. Franke).

The phosphorus ligand for the catalyst system of the invention is preferably a phosphine (e.g. TPP (triphenylphosphine)), a monophosphite (e.g. Alkanox 240 (tris (2,4-di-tert-butylphenyl)phosphite)) or a bisphosphite (e.g. BiPhePhos). It is also possible to use mixtures of ligands.

The hydroformylation is preferably carried out under the following conditions: The temperature in the hydroformylation is preferably within a range from 60 to 250° C., further preferably within a range from 70 to 225° C. and more preferably within a range from 80 to 210° C. The pressure in the hydroformylation is preferably within a range from 10 to 350 bar absolute, further preferably within a range from 30 to 325 bar absolute and more preferably within a range from 45 to 300 bar absolute.

According to the invention, the hydroformylation is performed in at least one reaction zone. A reaction zone for the purposes of the present invention comprises at least one reactor in which the hydroformylation is carried out. It is also possible for the reaction zone to comprise more than one reactor, in particular two or three reactors, which can be connected in parallel or in series or arranged in a hybrid of parallel and serial connection.

The pressure in the hydroformylation normally corresponds to the total gas pressure. The total gas pressure in the context of the present invention means the sum of the pressures occurring from all the gaseous substances present, that is to say the pressure of the (total) gas phase. In the present invention, this corresponds in particular to the sum of the partial pressures of $H_2$, i.e. the total gas pressure is then the syngas pressure. In the hydroformylation of the invention, the proportion of the partial pressure represented by either CO or $H_2$ constitutes not more than 70% of the total gas pressure, preferably not more than 65% of the total gas pressure, more preferably not more than 60% of the total gas pressure.

The liquid reaction output containing the product and obtained in the hydroformylation is accordingly also under the pressure present during the hydroformylation. Subsequently, in step b), a gas exchange is performed with the reaction output, which affords a liquid reaction output in which the partial pressure of CO or $H_2$ accounts for more than 90% of the total gas pressure, preferably more than 95% of the total gas pressure, more preferably more than 98% of the total gas pressure. The proportion of the partial pressure represented by either CO or $H_2$ is selectively increased by this gas exchange, while the proportion of the partial pressure represented by the respective other component is decreased. Possible processes for the gas exchange are known to those skilled in the art.

The gas exchange in step b) is effected, for example, by at least partially discharging the gas present, i.e. expanding the reaction output, and then injecting CO or $H_2$ until the desired proportion of the partial pressure represented by CO or $H_2$, that is to say more than 90% of the total gas pressure, preferably more than 95% of the total gas pressure, more preferably more than 98% of the total gas pressure, has been attained. This can be effected in one step or in multiple steps, i.e. the expansion of the liquid reaction output and the subsequent injection of CO or $H_2$ are effected in repeated succession. In another variant, the expansion of the output from the reaction is followed by injection of CO or $H_2$ using a mixing zone and/or a bubble column until the desired proportion of the partial pressure represented by CO or $H_2$, more than 90% of the total gas pressure, preferably more than 95% of the total gas pressure, more preferably more than 98% of the total gas pressure, has been attained. The gas phase obtained in the expansion in the gas exchange may be returned to the reactor.

The discharge of the gas/expansion of the liquid reaction output and the subsequent pressurization with CO or $H_2$, optionally using a mixing zone and/or a bubble column, can be conducted once or more than once in succession in order to set the desired partial pressure fraction. After the gas exchange, the total gas pressure is preferably 1 to 70 bar absolute, further preferably 2 to 30 bar absolute and more preferably 4 to 20 bar absolute. After the gas exchange, the reaction output is in the form of a pressurized liquid, where the proportion of the partial pressure of CO or $H_2$ accounts for more than 90% of the total gas pressure, preferably more than 95% of the total gas pressure, more preferably more than 98% of the total gas pressure. The pressurized reaction output is then kept under the pressure with the proportion of the partial pressure specified preferably for a certain period of at least 15 minutes, more preferably at least 30 minutes. The temperature is preferably 80° C., more preferably 100° C.

The gas exchange is followed, in step c), by a single-stage or multistage expansion of the liquid reaction output obtained from step b) to a pressure of less than 1 bar absolute, preferably less than 800 mbar absolute. The aim is to generate at least a slight vacuum in this step, in order to facilitate the thermal separation. The expansion of pressurized liquid phases, such as the reaction output obtained from step b), is known in principle to the person skilled in the art. For this purpose, for example, it is possible to use suitable expansion methods. The gas phase obtained in the expansion in step c) may be returned to the reactor.

The liquid reaction output expanded in step c) is sent to a thermal separation in the subsequent step d), in order to separate the reaction output into a low-boiling and a high-boiling fraction. The low-boiling fraction contains at least a portion of the aldehydes and may additionally contain alkanes and/or unconverted olefins. The high-boiling fraction contains the catalyst and may additionally also contain aldehydes or high-boiling compounds. Thermal separation in the context of the present invention means a separation process in which separation is effected on the basis of boiling point. Corresponding processes are sufficiently well known to the person skilled in the art. In a preferred embodiment of the present invention, the thermal separation comprises at least one thermal separation process selected from the group consisting of thin-film evaporation, distillation, flash evaporation, falling-film evaporation and short-path evaporation. The thermal separation is preferably conducted at a temperature of 20° C. to 200° C., preferably between 50° C. and 160° C.

The process according to the invention may in principle comprise further steps, provided that the general sequence is fundamentally maintained. For example, it is possible that the thermal separation is preceded or followed by performance of at least one membrane separation. Membrane separation processes can separate the homogeneous catalyst system from the remaining reaction output.

If a membrane separation follows the thermal separation in step d), the membrane separation is preferably conducted at a transmembrane pressure of 5 to 100 bar absolute, further preferably 10 to 80 bar absolute and more preferably 20 to 50 bar absolute. In a preferred embodiment, the membrane separation is also conducted at a temperature of 0° C. to 200° C., more preferably between 20° C. and 160° C.

The membrane material used in the membrane separation is preferably selected from the group consisting of poly(dimethylsiloxane)s, polyimides, partially fluorinated polymers, completely fluorinated polymers, perfluorinated polymers, amorphous fluoropolymers (e.g. Cytop®), amorphous or partially crystalline perfluoroalkoxy polymers (e.g. Hyflon®), block copolymers of the abovementioned materials, polymers having intrinsic microporosity (PIM), poly(aryletherketone)s, in particular poly(etheretherketone)s and poly(etherketoneketone)s, polybenzimidazoles and polyethers. Also suitable are polymers having intrinsic microporosity (PIMs) of diverse monomer composition, in particular those containing spirobifluorene groups. The membrane material is preferably a polydimethylsiloxane (PDMS) or a perfluoroalkoxy polymer such as Hyflon®.

In a preferred embodiment, the membrane material used is intrinsically stable in the reaction output/in the mixture present after the thermal separation, i.e. it does not require any additional crosslinking of the polymer chains.

It is further preferable when CO or $H_2$ is injected onto the residual reaction output depleted of the aldehydes formed, obtained from step d), until the partial pressure of CO or $H_2$ accounts for more than 90% of the total gas pressure, preferably more than 95% of the total gas pressure, more preferably more than 98% of the total gas pressure. Since the thermal separation is effected at a pressure of less than 1 bar, the corresponding proportion of the partial pressure can be achieved by using a corresponding gas or gas mixture in which the proportion of the partial pressure represented by CO or $H_2$ already exists, in order to inject it onto the residual reaction output obtained from step d).

The process of the invention may be performed continuously or batchwise. In a preferred embodiment, the process is performed continuously.

The present invention is elucidated hereinbelow with reference to examples. These examples do not however constitute any restriction, but serve only for illustration.

EXAMPLE

Example 1—Gas Exchange with CO

Dicarbonyl(acetylacetonato)rhodium(I) (about 200 ppm) as precursor for the transition metal of the catalyst system and the phosphorus ligand Alkanox® 240 (tris(2,4-di-tert-butylphenyl)phosphite)) were dissolved in 1-nonanol in a molar rhodium:ligand ratio of 1:20 and mixed well. A sample (1) of the solution thus produced was taken and analyzed for rhodium content. The remaining solution was introduced into a reactor pressurized to 25 bar absolute with CO at 150° C. for about 1 h, and then a vacuum of 300 mbar absolute was applied. Again, a sample (2) was taken and analyzed for rhodium content. Rhodium content was determined by ICP-MS (inductively coupled plasma mass spectrometry) analysis. The results are shown in Table 1.

TABLE 1

Rhodium content in samples 1 and 2

| Sample | Rhodium content/ppm |
| --- | --- |
| 1 (after making up the solution) | 195 |
| 2 (after injection of CO and vacuum) | 191 |

Example 2—without Gas Exchange

Dicarbonyl(acetylacetonato)rhodium(I) (about 200 ppm) as precursor for the transition metal of the catalyst system and the phosphorus ligand Alkanox® 240 (tris(2,4-di-tert-butylphenyl)phosphite)) were dissolved in 1-nonanol in a molar rhodium:ligand ratio of 1:20 and mixed well. A sample (3) of the solution thus produced was taken and analyzed for rhodium content. The remaining solution was introduced into a reactor pressurized to 25 bar absolute with synthesis gas at 150° C. for about 1 h, and then a vacuum of 300 mbar absolute was applied. Again, a sample (4) was taken and analyzed for rhodium content. Rhodium content was determined by ICP-MS (inductively coupled plasma mass spectrometry) analysis. The results are shown in Table 2.

TABLE 2

Rhodium content in samples 3 and 4

| Sample | Rhodium content/ppm |
| --- | --- |
| 3 (after making up the solution) | 199 |
| 4 (after injection of synthesis gas and vacuum) | 88 |

It is clearly apparent that the gas exchange with subsequent application of a vacuum leads to a distinct reduction in rhodium loss, i.e. the rhodium content in sample 2 from example 1 afterwards is much higher than in sample 4 from example 2.

Example 3—Gas Exchange with Hydrogen and Carbon Monoxide with a Subsequent Membrane Separation In this example, a membrane separation was conducted after the gas exchange, and the rhodium concentration in permeate and retentate stream was measured in order to determine the content of the catalyst system.

Dicarbonyl(acetylacetonato)rhodium(I) (1.97 g, 7.63 mmol) as precursor for the transition metal of the catalyst system and the phosphorus ligand Alkanox® 240 (tris(2,4-di-tert-butylphenyl)phosphite)) (98.74 g, 152.6 mmol) were dissolved in toluene (2612.1 g) in a molar rhodium:ligand ratio of 1:20 at an Rh concentration of 300 ppm by mass.

This solution was used to conduct a membrane separation in a membrane test apparatus with a closed circuit, with recycling of permeate and excess retentate back into the feed. The membrane material used was commercially available Borsig membrane (membrane type—poly(dimethylsiloxane)).

First of all, the catalyst was preformed at synthesis gas pressure 50 bar at 60° C. in the reactor without membrane separation. Thereafter, the reactor was decompressed to total gas pressure 20 bar, and then subsequently to 2 bar. The temperature was lowered to 30° C. and the flat channel test cells were put into operation. The membrane circuit was operated at 30° C. and feed pressure 50 bar and permeate supply pressure 20 bar.

The reactor was pressurized to 20 bar with synthesis gas ($CO:H_2$ mixture=about 50:50). Feed, retentate and permeate samples were taken and were analysed for their rhodium concentration by means of ICP-MS in order to ascertain the rhodium retention therefrom (rhodium retention=1−(Rh concentration in the permeate/Rh concentration in the retentate). The rhodium retention was 73% (measurement 1).

With continuing membrane separation, a gas exchange was then conducted, in which the reactor was repeatedly expanded to 2 bar and subsequently pressurized again with hydrogen to 20 bar. This pressure exchange consisting of expanding and injecting hydrogen was repeated three times. Subsequently, measurement 2 was conducted with a hydrogen feed. Samples were taken both of the feed and of the permeate and analysed for their rhodium concentration, in order to ascertain the rhodium retention therefrom. The rhodium retention after the injection of hydrogen was 80%. It was found that the retention of rhodium in membrane separation can be distinctly increased as a result of the prior contacting with hydrogen rather than synthesis gas.

Subsequently, similarly to the gas exchange of synthesis gas to hydrogen, the reverse gas exchange back from hydrogen to synthesis gas pressure was conducted in order to re-establish the starting point (measurement 3). The rhodium retention thereafter was 70%.

Thereafter, in a similar manner, another gas exchange was conducted, this time conducting the gas exchange to carbon monoxide (measurement 4). The rhodium retention thereafter was 78%. The results are shown in Table 3.

TABLE 3

Overview of the retention of rhodium in measurements 1 to 4

| Measurement | Rhodium retention of membrane |
| --- | --- |
| 1 (after insertion of the solution and synthesis gas) | 73% |
| 2 (after pressurization with hydrogen) | 80% |
| 3 (after pressurization with synthesis gas) | 70% |
| 4 (after pressurization with carbon monoxide) | 78% |

It was again found that the retention of rhodium can be distinctly increased even in the case of downstream membrane separation as a result of the prior contacting with carbon monoxide or hydrogen rather than synthesis gas. It can thus be shown that gas exchange both with hydrogen and with carbon monoxide leads to a distinct reduction in rhodium loss.

The invention claimed is:

1. A process for preparing an aldehyde, the process comprising at least:
   a) reacting, in a hydroformylation, at least one $C_2$ to $C_{20}$ olefin with synthesis gas in the presence of a homogeneously dissolved catalyst system comprising at least one metal from the group consisting of Co and Rh, and a phosphorus ligand; wherein the hydroformylation is conducted in at least one reaction zone and at a pressure of 10 to 350 bar absolute, which affords a first liquid reaction output containing at least the aldehyde and unconverted olefins, and wherein a partial pressure of CO or $H_2$ accounts for at most 70% of a total gas pressure of all gaseous substances present;
   b) performing a gas exchange with the first liquid reaction output, which affords a second liquid reaction output in which the partial pressure of CO or $H_2$ accounts for more than 90% of the total gas pressure;
   c) expanding the second liquid reaction output obtained from b) in a single-stage or multistage expansion, to a pressure of less than 1 bar absolute, which affords a third liquid reaction output; and
   d) feeding the third liquid reaction output obtained from c) to a thermal separation in order to separate the third liquid reaction output into a low-boiling fraction and a high-boiling fraction, with the low-boiling fraction containing at least a portion of the aldehyde.

2. The process according to claim 1, wherein the hydroformylation in a) is conducted at a pressure of 15 to 350 bar absolute.

3. The process according to claim 1, wherein the homogeneously dissolved catalyst system in a) comprises at least Rh and the phosphorus ligand.

4. The process according to claim 1, wherein the gas exchange in b) is effected by expanding the first liquid reaction output and subsequently injecting CO or $H_2$ until a desired partial pressure of CO or $H_2$ is attained.

5. The process according to claim 4, wherein the expansion of the first liquid reaction output and the subsequent injection of CO or $H_2$ are effected in repeated succession.

6. The process according to claim 1, wherein the hydroformylation is conducted at a temperature of 80° C. to 250° C.

7. The process according to claim 1, wherein the total gas pressure after the gas exchange is 1 to 70 bar absolute.

8. The process according to claim 1, wherein the thermal separation is conducted at a temperature of 20° C. to 200° C.

9. The process according to claim 1, wherein the thermal separation comprises at least one thermal separation process selected from the group consisting of thin-film evaporation, distillation, flash evaporation, falling-film evaporation, and short-path evaporation.

10. The process according to claim 1, wherein the process is conducted continuously.

11. The process according to claim 1, wherein the at least one reaction zone comprises at least one reactor.

12. The process according to claim 1, wherein the thermal separation is preceded or followed by performance of at least one membrane separation.

13. The process according to claim 12, wherein the thermal separation is followed by injection of CO or $H_2$ onto a liquid reaction output depleted of the aldehyde until the partial pressure of CO or $H_2$ accounts for more than 90% of the total gas pressure.

14. The process according to claim 12, wherein a membrane material in the at least one membrane separation is selected from the group consisting of poly(dimethylsiloxane)s, polyimides, partially fluorinated polymers, completely fluorinated polymers, perfluorinated polymers, amorphous fluoropolymers, amorphous or partially crystalline perfluoroalkoxy polymers, block copolymers of the above-mentioned materials, polymers having intrinsic microporosity, poly(aryletherketone)s, polybenzimidazoles, and polyethers.

15. The process according to claim 14, wherein the membrane material is intrinsically stable in a reaction output or in a mixture present after the thermal separation.

16. The process according to claim 1, wherein in b), the partial pressure of CO or $H_2$ accounts for more than 98% of the total gas pressure.

17. The process according to claim 7, wherein the total gas pressure after the gas exchange is 4 to 20 bar absolute.

18. The process according to claim 8, wherein the thermal separation is conducted at a temperature between 50° C. and 160° C.

19. The process according to claim 13, wherein the partial pressure of CO or $H_2$ accounts for more than 98% of the total gas pressure.

20. The process according to claim 14, wherein the membrane material is a poly(etheretherketone) or a poly(etherketoneketone).

* * * * *